(12) United States Patent
Mandecki

(10) Patent No.: US 6,440,700 B1
(45) Date of Patent: Aug. 27, 2002

(54) METHOD OF COMBINATORIAL PROTEIN SYNTHESIS BASED ON RIBOSOMAL FRAMESHIFTING

(76) Inventor: Wlodek Mandecki, 22 Arnold Dr., Princeton Junction, NJ (US) 08550

( * ) Notice: Subject to any disclaimer, the term of this patent is extended or adjusted under 35 U.S.C. 154(b) by 0 days.

(21) Appl. No.: 09/640,340

(22) Filed: Aug. 16, 2000

(51) Int. Cl.[7] .......................... C12P 21/06; C12Q 1/68; C12N 15/74
(52) U.S. Cl. .......................... 435/69.1; 435/6; 435/489
(58) Field of Search ........................ 435/69.1, 6, 252.3, 435/254.11, 320.1, 325, 489; 530/350

(56) References Cited

PUBLICATIONS

M.W. Ravera et al., "Identification of an allosteric binding site on the transcription factor p53 using a phage–displayed peptide library", *Oncogene* (1998) 16:1993–1999.

H.B. Lowman, "Bacteriophage Display and Discovery of Peptide Leads for Drug Development", *Annu. Rev. Biophys. Biomol. Struct.* 1997, 26:401–24.

Juan Carcamo et al., "Unexpected frameshifts from gene to expressed protein in a phage–displayed peptide library", *Proc. Natl. Acad. Sci. USA,* vol. 95, pp. 11146–11151, 9/98, Biochemistry.

Emanuel Goldman et al., "Efficiencies of translation in three reading of unusual non–ORF sequences isolated from phage display", *The FASEB Journal,* vol. 14, Mar., 2000, pp. 603–611.

Thomas P. Hopp et al., "A Short Polypeptide Marker Sequence Useful for Recombinant Protein Identification and Purification", *Biotechnology,* vol. 6, Oct., 1988, pp. 1204–1210.

Timothy J. Bolling et al., "An *Escherichia coli* Expression Vector fo High–Level Production of Herterologous Proteins in Fusion with CMP–KDO Synthetase", *BioTechniques,* vol. 8, No. 5, (1990), pp. 488–490.

W. Mandecki et al., "FokI method of gene synthesis", *Gene,* 68 (1988) pp. 101–107.

Wlodek Mandecki et al., "A Mathematical Model for Biopanning (Affinity Selection) Using Peptide Libraries on Filamentous Phage", *J. theor. Biol.* (1995) 176, pp. 523–530.

Oded Livnah et al., "Functional Mimicry of a Protein Hormone by a Peptide Agonist: The EPO Receptor Complex at 2.8A", *Science,* vol. 273, Jul. 26, 1996, pp. 464–471.

Nicholas C. Wrighton et al., "Small Peptides as Potent Mimetics of the Protein Hormone Erythropoietin", *Science,* vol. 273, Jul. 26, 1996, pp. 458–463.

Steven E. Cwirla et al., "Peptide Agonist of the Thrombopoietin Receptor as Potent as the Natural Cytokine", *Science,* vol. 276, Jun. 13, 1997, pp. 1696–1699.

Stephen D. Yanofsky et al., "High affinity type I interleukin 1 receptor antagonists discovered by screening recombinant peptide libraries", *Proc. Natl. Acad. Sci. USA,* vol. 93, pp. 7381–7386, Jul. 1996, Pharmacology.

Jamie K. Scott et al., "Searching for Peptide Ligands with an Epitope Library", *Science,* vol. 249, Jul. 27, 1990, pp. 386–390.

*Primary Examiner*—Remy Yucel
*Assistant Examiner*—Konstantha Katcheves
(74) *Attorney, Agent, or Firm*—Brinks Hofer Gilson & Lione

(57) ABSTRACT

Disclosed are materials and methods for practicing combinatorial protein synthesis based on ribosomal frameshifting. The genes, encoding the proteins to be synthesized, are constructed by assembly of several double-stranded DNA fragments and are cloned into bacteria. The genes include interspersed frameshifting sequences. Proteins are made in the cell by translating nucleotide sequences in a combinatorial mode. The invention can be used for the selection of new, modified or improved proteins.

21 Claims, 7 Drawing Sheets

Switch

Splitter

Mixer

Frame 0  ┤Epitope├                    ┤Gene III├ Frame 0
+1                                                  +1
-1                                                  -1

┤Insert├

B                                          2

┤Epitope├                    ┤Gene III├

C                                          3

┤Epitope├                    ┤Gene III├

FIG. 7

Step 1: Vector Construction

Phagemid Type A1

```
     SfiI                              FLAG               BglII            KpnI         NotI
TATGGGGCCCAGCGGCCGCCATGGCCGACTACAAAGACGATGACGACAAA AGATCT....... GGTACC GCGGCCGCAGGTGCGCCGGTG
ATACCCCGGGTCGCCGGCGGTACCGGCTGATGTTTCTGCTACTGCTGTTT TCTAGA....... CCATGG CGCCGGCGTCCACGCGGCCAC
     Tyr Ala           Met Ala                                                         Gly Ala Pro Val
     Signal                                            Stuffer                              Gene III
     Peptide
```

Phagemid Type A2    ...GGTACC      AAGCGGCCGC....
                   ...CCATGG      TTCGCCGGCG....

Phagemid Type A3    ...GGTACC      AGCGGCCGC....
                   ...CCATGG      TCGCCGGCG....

Step 2: Library Construction

Phagemid 1

```
FLAG  BglII                       KpnI     NotI
Asp Lys
GACAAA AGATCT ....... GGTACC GCGGCCGC
CTGTTT TCTAGA ....... CCATGG CGCCGGCG
              Stuffer           Gene III
```

↑ Cut with BglII and KpnI

Linearized Phagemid DNA

GACAAA A                C GCGGCCGC
CTGTTT TCTAG         CATGG CGCCGGCG

Synthetic Oligo
GATCT $N_k$ GGTAC
5'

↓ Extension with DNA Polymerase

GACAAA AGATCT $N_k$ GGTACC GCGGCCGC
CTGTTT TCTAGA $N_k$ CCATGG CGCCGGCG

Circularized Phagemid Library DNA

GACAAA AGATCT $N_k$ GGTACC GCGGCCGC
CTGTTT TCTAGA      CCATGG CGCCGGCG
                                  3'

→ Ligate

METHOD OF COMBINATORIAL PROTEIN SYNTHESIS BASED ON RIBOSOMAL FRAMESHIFTING

BACKGROUND OF THE INVENTION

The present invention relates to a type of protein synthesis utilizing combinatorial translation of a single gene sequence interspersed with programmed ribosomal frameshifting sequences. Specifically this type of protein synthesis can be utilized to make numerous, varied proteins from a single gene. More particularly, libraries can be made utilizing this combinatorial protein synthesis and the libraries can then be used to screen for specific protein activities.

Unusual translational events, such as frameshifting, are known to play an important role in some diseases. For example, expression of the enzyme, reverse transcriptase, utilized by many retroviruses including HIV, involves a naturally occurring translational frameshift. Frameshifted gene expression is also thought to play a role in some forms of colon cancer, Alzheimer's disease, and hemophilia A.

Rapid progress in sequencing genomes, as well as in genomics, proteomics and related disciplines has created a great number of targets for drug discovery and other potential treatments for various diseases. Specifically, phage libraries have proved invaluable in identifying peptide ligands of therapeutic value. For example, Yanofsky et al. (1996) described the isolation of a monomer peptide antagonistic to interleukin 1 (IL-1) with nanomolar affinity for the IL-1 receptor. Similarly, Wrighton et al. (1996) and Livnah et al. (1997) reported peptides that bind to the erythropoetin (EPO) receptor. Likewise Cwirla et al. (1997) described the identification of two families of peptides that bind to the human thrombopoietin (TPO) receptor. More particularly, there has been considerable progress in both construction and use of phage libraries over the last few years. For example, library diversity has been continually increasing, from $10^8$ (Scott and Smith, 1991) to up to $10^{11}$ more recently. The number and types of protein molecules displayed as well as the types of libraries have increased, while the selection methods have also continued to improve (reviewed by Lowman, 1997).

One such improved selection method, called biopanning, is the selection of peptides or proteins with specific desired binding properties. In contrast to traditional sequence based discovery methods, biopanning enables screening rates that are 10,000 times faster. This technique involves the immobilization of a target protein on a solid phase, incubation of a phage library with the solid phase to allow phage binding to the target, followed by washes of unbound phage and elution of the bound phage. The eluted phage is grown in *Escherichia coli*. Typically, several rounds of biopanning (2 to 6) are performed to identify clones of interest. These clones of interest are capable of producing or expressing the protein which may have significant utility in the production of commercial therapeutic products, industrial proteins, research reagents or consumer protein enriched products.

Though several successes in drug discovery have arisen through use of a phage library, there are different types of libraries suitable for this type of search. For example, other than the phage library, researchers often rely on combinatorial libraries. The term "combinatorial library" typically refers to libraries of biomolecules. Each element of the combinatorial library is composed of a string of several building blocks. The number of building blocks can be anywhere from 2 to 100 or even much more. Varying the building blocks at different positions within the string generates the diversity of the combinatorial library. Thus, if the string length is 5, and the number of building blocks is 10, the number of possible biomolecules in the combinatorial library is $10^5$. This is the potential diversity of the library. The observed diversity, which is the number of biomolecules actually constructed, can be less or be equal to the potential diversity.

An example of a combinatorial library is the library of random peptides on filamentous phage. The typical length of the peptide in such a library is 15 amino acid residues, and the number of building blocks (amino acids) is 20. Thus, the potential diversity of the library is $20^{15}=3\times10^{19}$. In practice, the number of *Escherichia coli* cells used to construct such a library acts as a limit on the actual diversity of the library. Thus, the observed diversity of the library is rarely above $10^{11}$.

There are many other examples of combinatorial libraries, including libraries of small organic molecules, phage libraries of antibodies, or libraries of genes obtained by DNA shuffling. Yet in all cases of gene libraries, be the library a phage library, a combinatorial library or another type of library, expression of a single gene in the library results in only one type (sequence) of protein being translated or produced.

Despite many successes in using phage display via libraries and biopanning, researchers still strive for even larger libraries and faster protocols in their search for a peptide or protein ideally suited for an envisioned task. Often, as part of this search, there is a need to screen a variety of proteins and ultimately select only those with the most desirable properties. As stated earlier, one problem with conventional libraries is that each gene encodes only one type of a protein, or corresponds to only one protein sequence. The following example illustrates this problem. *Escherchia coli* can make and store up to $10^7$ protein molecules in a single cell. Researchers can engineer an *Escherichia coli* cell for expression of a single heterologous gene and that cell can then produce up to 70% (or even more) of that number of proteins ($10^7$) as identical copies of the protein encoded by that gene. This is highly desirable when large quantities of a protein are needed. However, if the researcher is attempting to make a large number of varied proteins for the purpose of screening the proteins to find the ones with the most desired properties, then having huge amounts of a single type of protein is inefficient and wasteful. As a result, there is a critical need in the art for a way to synthesize larger libraries of more varied proteins.

The present invention overcomes this difficulty by inserting ribosomal frameshifting sequences into the gene sequence of interest to cause combinatorial translation of the gene sequence so that the single sequence yields a multitude of different peptides. By causing the reading frame switch, ribosomal frameshifting sequences affect the amino acid sequence of the protein made by the ribosome. Therefore, insertion of a ribosomal frameshifting sequence into a gene causes that gene to code for significantly more than the traditional one peptide or protein.

The initial and most widely recognized presumption in considering DNA sequences for expression potential is the requirement for an open reading frame. Surprisingly, in a previous drug discovery protocol by the inventor, a large number of sequences expressed in a random peptide library were found to contain non-open reading frame (non-ORF) and frameshifted sequences (Carcamo et al., 1998). The study was designed to isolate peptides capable of binding to growth hormone binding protein (GHBP). Originally, in biopanning experiments for the specific protein targets, namely GHBPS, the inventor expected an open reading frame (ORF) corresponding to the full length of the peptide and an epitope tag that followed. However, the inventor was surprised to observe this class of sequence in only about 50% of all sequences identified in biopanning as binding to the target (Ravera et al., 1998). Even more surprisingly, the inventor observed two other types of sequences that were, qualitatively, very different from the sequence originally expected. These two sequences contained a frameshift in the +1 or −1 direction but were, also unexpectedly, capable of expression.

One non-ORF phage clone, known as H10, which is capable of binding to the rat growth hormone binding protein (GHBP), was studied further. More specifically, a secondary peptide library containing random mutations of this sequence was constructed and panned against GHBP in an attempt to optimize and correct the reading frame (Carcamo et al., 1998). While the study did not correct the reading frame of the H10 clone, it did yield clones capable of binding to the GHBP. The major focus of this study was the regulation of receptor function with surrogate peptide ligands in attempt to aid in developing new therapies for diseases such as acromegaly and dwarfism. The discovery of expression of non-ORF clones was a surprising result of this study.

One advantage of the present invention is the ability to synthesize multiple, varied proteins from a single genetic sequence. Creating a library of phages carrying the programmed ribosomal frameshifting sequences, as in the present invention, allows the researcher access to a much larger, more varied library of proteins, capable of providing a more efficient search for a therapeutic protein, or any other protein of interest. Furthermore, a library of genes containing frameshifting sequences gives the researcher a tool for understanding the rules and mechanisms of gene expression, an understanding that is especially important in this era of genome sequencing. For the foregoing reasons, there is a critical need in the art for a method of synthesizing a variety of proteins from a single gene or genetic source.

BRIEF SUMMARY OF THE INVENTION

Traditionally, a single gene codes for a single protein. In one aspect, the present invention provides a method for the combinatorial synthesis of proteins, allowing the synthesis of several proteins using the genetic information of just one gene. The present invention accomplishes combinatorial protein synthesis by utilizing nucleic acid sequences known as frameshifting sequences. Placing one or more of these frameshifting sequences within a recombinantly made gene allows the ribosome to switch reading frames during translation, thereby producing many types of proteins rather than a single type.

In another aspect, the present invention enables the construction of a new type of phage in which the phage-displayed protein is encoded by a gene having alternating frameshifting and random nucleic acid sequences. Thus, an advantage of the present invention is that a single E. coli cell is programmed to make significantly more than one type of recombinant polypeptide per cell. The design of such library is based on the finding that the ribosome is able to partially switch reading frames when translating sequences in phage libraries, and can do it with a high frequency in many types of clones (Carcamo et al., 1998; Goldman et al., 2000). The frame switch occurs on short frameshifting sequences, often involving a stop codon. Thus, instead of having one peptide made from a single gene, the cell can make several peptides by translating mRNA originating from a single gene and switching reading frames in the process. The number of possible translation routes grows exponentially with the number of the frameshifting sequences. The method of the present invention can be used to increase the diversity of protein libraries, select for novel proteins and to improve biological properties of proteins.

In another aspect, the present invention provides a method for detecting a protein from a library of combinatorial proteins by utilizing biopanning techniques to select or screen for the protein that binds to the target biomolecule.

I. Definitions

By "coat protein" is meant the protein which serves as an element of the outer surface of a phage. Coat proteins form a type of envelope around the phage particle and could be considered surface proteins.

By "complementary DNA (cDNA)" is meant any DNA molecule that is reverse transcribed from an RNA template.

By "detecting the presence of a peptide" is meant screening or selecting for a peptide having predefined properties. The skilled artisan may choose between various technologies in screening or selecting for a peptide. Some examples of techniques that might be used include biopanning against a specific antibody, screening by sequencing, and the antibiotic resistance-based selection.

By "DNA" is meant a nucleic acid in which the sugar is deoxyribose as opposed to ribose in RNA. DNA is intended to include any nucleic acid which can be transcribed to yield RNA.

By "enzymatic activity" is meant the actions or results produced by an enzyme, which is understood as a complex protein capable of catalyzing specific biochemical reactions.

By "expressing" is meant that the sequence encoded by the polynucleotide is transcribed and translated into the corresponding peptide, polypeptide or protein. It is further understood that expressing means the translated product may appear as a fusion product to the coat protein of the phage carrying the sequence, it may appear in the cytoplasm of the bacterial host cell or it may appear on the outer cell membrane of the bacterial host cell. It is also understood that in certain preferred embodiments, "expressing" means only the transcription of the DNA into the complementary RNA sequence or only the translation of RNA into the complementary peptide.

By "filamentous phage vector" is meant a vector based on filamentous phage which is useful in phage display systems. By inserting the coding sequence of interest into the coat protein gene of the filamentous phage vector, the skilled artisan is able to construct a fusion protein that is expressed or displayed as part of the coat protein of the phage particle.

By "fusion protein" is meant a protein produced from the translation of a genetic sequence and an inserted, or placed in the immediate vicinity, another genetic sequence.

By "gene III" is meant the gene encoding the minor coat protein of the M13 bacteriophage. The M13 bacteriophage is composed of 10 genes and gene III codes for the minor coat protein, also known as the pill protein.

By "genomic DNA" is meant any DNA sequence found within a genome.

By "heterologous promoter" is meant a foreign or synthetic DNA sequence capable of initiating transcription of the downstream DNA sequence into the complementary RNA sequence. Foreign or synthetic simply means that the sequence is derived from another species or engineered by one skilled in the art.

By "isolating" is meant separating the sequence, peptide, polypeptide or protein of interest from other cellular materials. Isolation of a sequence, peptide, polypeptide or protein of interest is a common and well understood technique in the art and there are many methods available to one skilled in the art to achieve isolation of a target molecule. For example, the skilled artisan may use selection techniques where only cells expressing the target molecule can survive, or a targeted protein may be isolated from a solution by taking advantage of its binding properties, molecular weight or some other unique feature of the target protein.

By "library" is meant a collection of biomolecules, such as peptides, some of which may exhibit biological activity or other activity.

By "messenger RNA" is meant a nucleic acid in which the sugar is ribose as opposed to deoxyribose in DNA. Messenger RNA is intended to include any nucleic acid which can be entrapped by ribosomes and translated into protein. Further mRNA is understood to be the product of transcription and splicing.

By "microorganism" is meant any bacteria or bacteriophage capable of serving as host to the expression vector carrying the polynucleotide sequence of the present invention. The microorganism is also understood as being capable of amplifying the number of vectors carrying the polynucleotide sequence as well as expressing the peptides encoded by this sequence. In a preferred embodiment of the invention, *Escherichia coli* is used as the host microorganism. In the present invention, *Escherichia coli* is infected with phage carrying the polynucleotide sequence of the invention and the infection causes the *Escherichia coli* to produce and/or secrete the peptide fusion product of the present invention.

By "operably linked" is meant that a regulatory sequence, for example a promoter, is connected to a polynucleotide or genetic sequence in such a way as to permit expression of the gene product under the regulatory control of the attached promoter sequence.

By "origin of replication" is meant a polynucleotide sequence at which replication is initiated. Without an origin of replication, a vector or phage, cannot replicate and a colony of transformed cells could never be achieved. Origins of replication are commercially available, and one skilled in the art can use common techniques to insert a chosen origin of replication into a specific vector. One such technique might involve the use of restriction nucleases to form a specific cleavage and ligation site.

By "outer surface of a microorganism" is meant the extra-cellular membrane.

By "peptide" is meant any chain of amino acids, linked by a peptide bond, regardless of length or post-translational modifications such as glycosylation or phosphorylation. Peptide could also be interpreted to mean polypeptide, which only requires that there be more than two amino acids linked by a peptide. Further, the term peptide includes protein, polypeptide and peptides that can be expressed as translational products from mRNA.

By "phage" is meant a naturally occurring or engineered bacterial virus. Phage is not limited to a single type, but, for example, the phage of the invention could be engineered from any of the following known phage vectors including but not limited to; M13, lambda, Mu and P1. There are also different classes of phages suitable for construction of the phage of the present invention. More specifically, the filamentous phage is a preferred phage to display the combinatorial protein library of the present invention.

By "phagemid" is meant a filamentous phage vector the essential two elements of which are (a) the gene III, which produces the minor coat protein, pIII, and (b) the phage origin of replication. One example of a phagemid that can be used to practice the present invention is the pCANTAB5E phagemid.

By "polynucleotide" is meant a molecule, or a sequence, composed of more than one nucleotide and preferably more than 7 nucleotides, of either ribonucleic acid (RNA) or deoxyribonucleic acid (DNA) type. The term should be understood to include, as equivalents, derivatives, variants and analogs of either RNA or DNA made from nucleotide analogs, and, as applicable to the embodiment being described, single (sense or antisense) and double-stranded polynucleotides. The polynucleotide of the present invention is understood to contain ribosomal frameshifting sequences interspersed between coding genetic sequences. Further it is understood that the polynucleotide sequence encodes sequences, which when in mRNA form are known as ribosomal binding sites. A ribosomal binding site is a nucleic acid sequence recognized by the small subunit of the ribosome as the site for initiation of translation of a nucleic acid sequence. The large subunit of the ribosome binds to the ribosomal binding site after the small subunit has bound itself. Still further it is understood that the unique attribute of the polynucleotide sequence is its ability to produce a plurality of peptides from a single gene or genetic sequence.

By "plurality of peptides" is meant more than one peptide, where the peptides are composed of varying amino acid sequences.

By "selectable marker" is meant a gene insertion with a specific characteristic, used to distinguish cells that have taken up the vector from those cells that have not. For example, it is a well known technique in the art to insert an antibiotic resistance gene as a selectable marker. The cells harboring the vector are then grown on a medium containing the specific antibiotic. Thus only transformed cells, or those carrying the inserted gene and the selectable marker gene (antibiotic resistance gene) will be able to grow in the medium.

By "transformed microorganism" is meant any microorganism expressing a peptide or protein from the polynucleotide insert of the expression vector that transformed the microorganism. There are several different techniques available to one skilled in the art for creating a transformed microorganism. Some of these techniques would include the use of plasmid, phage, or phagemid to insert the polynucleotide sequence of the invention into the genome of the transformed microorganism.

By "vector" is meant a replicable nucleic acid construct, namely a plasmid, phage, phagemid or viral nucleic acid. Vectors may be used to amplify and/or express nucleic acid encoding a fusion peptide. In an expression vector, the nucleic acid sequence encoding a peptide of interest is operably linked to suitable control sequences capable of effecting expression of the peptide in a cell. The need for such control sequences will vary depending upon the cell selected and the transformation method chosen. Generally, control sequences include a transcriptional promoter, suitable mRNA ribosomal binding sites, and sequences that control the termination of transcription and translation. Methods that are well know to those skilled in the art can be used to construct expression vectors containing appropriate transcriptional or translational control signals. See for example, the techniques described in Sambrook et al., 1989, Molecular Cloning: A Laboratory Manual ($2^{nd}$ Edition), Cold Spring Harbor Press, N.Y., which are herein incorporated by reference.

Other features and advantages of the invention will be apparent from the following detailed description of the invention and from the claims.

BRIEF DESCRIPTION OF SEVERAL VIEWS OF THE DRAWINGS

FIGS. 4a, 4b, 4c. Vectors for selection of the frameshifting sequences. The selection of the insert frameshifting sequence of a given type is done by placing the insert between the upstream sequence containing the epitope tag (A, B or C), and the downstream sequence containing the gene III. Thus, e.g., vector A2 is used to select insert sequences capable of switching the ribosomes arriving in frame 0 to frame +1. Nine different types of the vectors are possible (=3×3).

FIG. 7. Graphical representation of the molecular cloning procedures. Rectangles highlight recognition sequences of SfiI and NotI restriction endonucleases. Cleavage sites on the top DNA strands are indicated by small black triangles. A detailed description is provided in the body of the patent application. SEQ ID Nos:1–13.

DESCRIPTION OF THE INVENTION

I. Polynucleotide Sequence of the Invention

Figure 1:
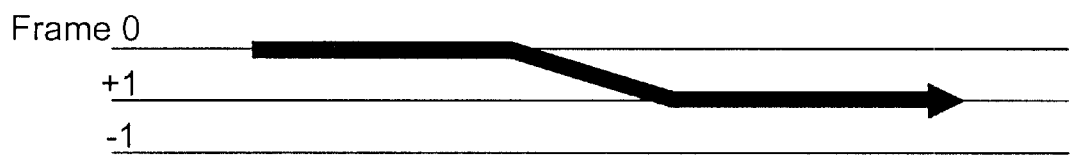
FIG. 1. Definitions of three types of frameshifting sequences. Arrows indicate relative translation rates in different reading frames. The top line in each panel represents translation in the 0 frame, the second line, translation in the +1 frame, and the third line, translation in the −1 frame.
Figure 1:
Figure 1:
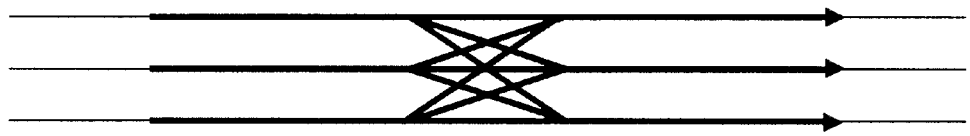

It is not unlikely that a minority of genes in all organisms rely on some form of "recoding" for translation of the mRNA sequence. "Recoding" is a general term used to describe non-canonical translational events caused by special mRNA sequences recognized by the ribosome. These special mRNA sequences are engineered into the present invention and termed "ribosomal frameshifting sequences". Normally the ribosome reads mRNA in successive, adjacent three nucleotide (triplet) codons. However, when the ribosome encounters one of these "recoding" or "ribosomal frameshifting" sequences, the ribosome deviates from the normal reading pattern. Characterization of this deviation includes but is not limited to skipping a nucleotide (a+1 frameshift), moving back on the mRNA molecule by one nucleotide (a−1 frameshift), or read through a termination codon (readthrough).

Ribosomal frameshifting is a frequent strategy used in the expression of viruses, pathogens, genetic elements and some genes. The present invention takes advantage of this strategy and utilizes it to cause a specific sequence of interest to undergo frameshifting, thereby enabling the production of a plurality of peptides from a single genetic sequence of interest. The knowledge gained from the present invention can aid not only in demonstrating novel functions of genes and genomes, but also in understanding processes of bacterial or viral infection, which could aid in disease prevention and management.

One of ordinary skill in the art will appreciate that the common presumption in considering DNA sequences for expression potential is the requirement for an open reading frame, starting with a methionine codon and ending with one of the three canonical stop codons. Several exceptions to this presumption have been discovered through the years. For example, it is now commonly Known throughout the art that some RNAs undergo post-transcriptional splicing. More recently, phenomena such as RNA editing and translational recoding have been observed. A preferred embodiment of the claimed invention, the polynucleotide sequence with ribosomal frameshifting sequences inserted, involves engineering a genetic sequence of interest to contain one or more of these exceptions to the aforementioned presumption.

In previous work involving biopanning experiments against several protein targets, the inventor isolated a large number of sequences from a random peptide library by phage display technology during drug discovery protocols. These isolated sequences were found to contain non-open reading frames (non-ORF) and frameshifted sequences, but were surprisingly being expressed nonetheless. (Carcamo et al., 1998; Mandecki et al., 1997; Ravera et al., 1998). This work was discussed under the Background of the Invention heading and is discussed briefly below.

The subject of this previous work was finding peptide ligands capable of binding to growth hormone binding proteins (GHBP). A surprising phenomena was observed during this work, namely the expression of genes without an open-reading frame. One clone capable of expression without an open reading frame (meaning that the expression product of the gene was capable of binding to rat GHBP even though the gene did not have an open reading frame), H10, was selected for further study, as mentioned above. Most importantly, the H10 clone was studied further in an attempt to correct the reading frame. DNA sequencing of the H10 clone sequence revealed two in-frame TGA-stop codons upstream of the sequence encoding the E-tag epitope (and the fusion to M13 gene III protein) in the same reading frame. A secondary peptide library on filamentous phage, designed to average ~4 mutations per sequence, was obtained by a doped mutagenesis procedure and again subjected to biopanning against the rat GHBP target. Again an unexpected result was obtained in that a number of additional clones were obtained, most of which exhibited frameshifts, both +1 and −1, in the placement of the E-tag sequence relative to the translation start, as well as retention of the 5' proximal TGA stop codon of parental H10. Because the 3' proximal third of the sequence yielded almost no mutations after phage display selection, it was possible to infer the amino acid sequence (and hence the reading frame) of the portion of the peptide fragment, which did in fact display the appropriate binding properties.

It is understood that SEQ ID NO: 1 is only one example of a sequence that demonstrates the ribosomal frameshifting sequence of the invention. It is further understood that there are numerous other sequences that may be utilized in practicing the present invention. The inventor appreciates that there are numerous other sequences, capable of causing ribosomal frameshifting, which may be engineered into the polynucleotide sequence of the present invention.

A. Ribosomal Frameshifting Sequences

In the present invention, a ribosomal frameshifting sequence is understood as any sequence on which any type of ribosbmal reading frame change occurs, including but not limited to a switch, splitter, mixer (all three are defined below), hopper, translation recoding, and ribosomal slippage. In a preferred embodiment of the invention, a switch frameshifting sequence is a nucleotide sequence that forces the ribosome to switch the reading frame when the ribosome encounters this sequence in the process of translating the mRNA. FIG. 1 depicts the translational pathway of a switch frameshifting sequence.

In another preferred embodiment, a splitter frameshifting sequence is a nucleotide sequence that forces the ribosome to choose between two or three reading frames when the ribosome encounters such a sequence in the process of translating the mRNA. FIG. 1 depicts the translational pathway of a splitter frameshifting sequence.

In yet another preferred embodiment, a mixer frameshifting sequence is a nucleotide sequence that forces the ribosome entering the sequence in any of three (or two) reading frames to switch the reading frames in such a way that the ribosome may leave the mixer sequence in any of the three (or two) outgoing reading frames. FIG. 1 depicts the translational pathway of a mixer frameshifting sequence.

1. Method for Selecting for Ribosomal Frameshifting Sequences

Figure 5:
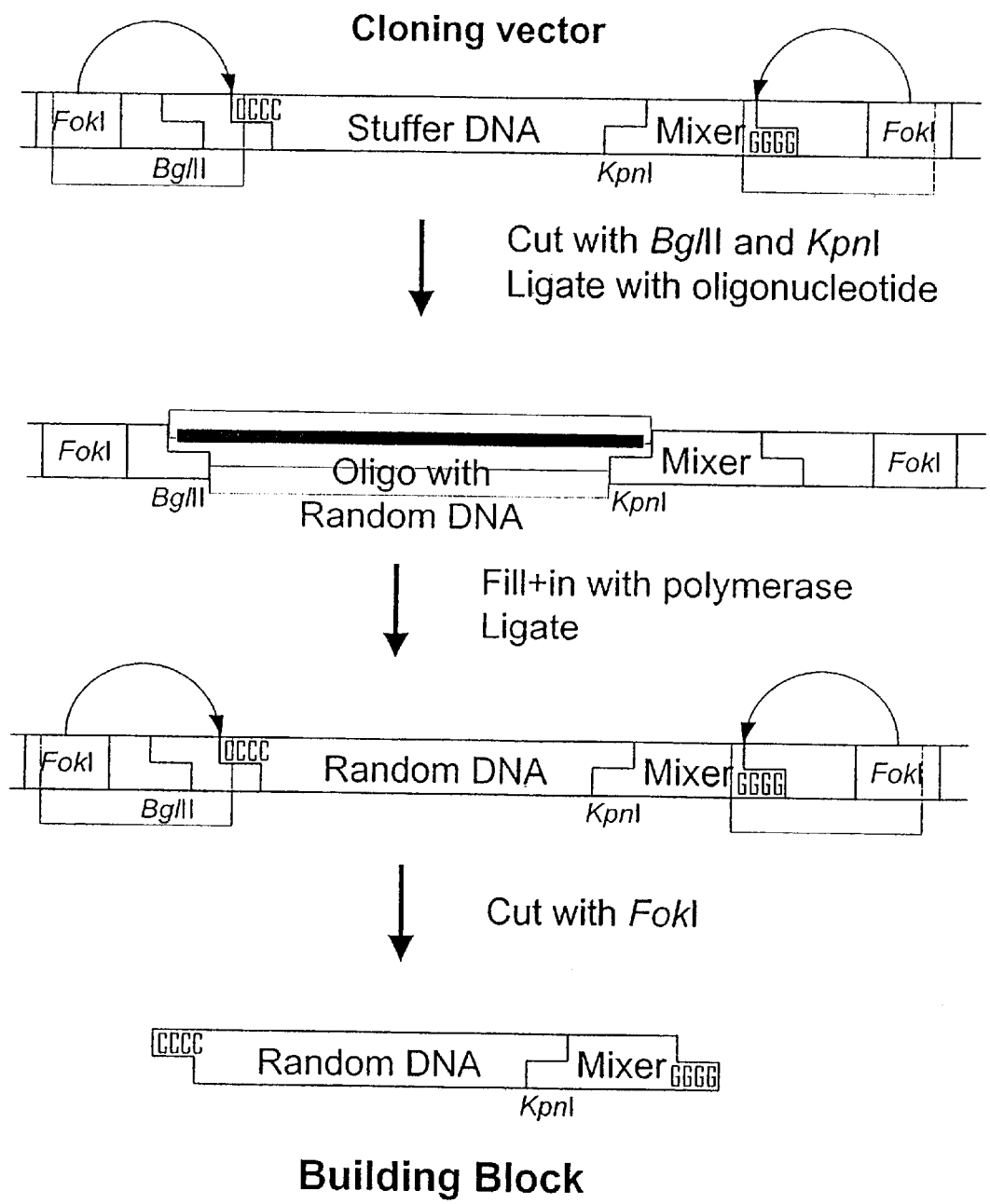
FIG. 5. Combinatorial assembly. A scheme for cloning random coding DNA into the cloning vector.

A preferred embodiment of the invention takes advantage of several of these frameshifting sequences by inserting a frameshifting sequence between other coding sequences in a gene. In another embodiment of the invention, the frameshifting sequence is used to separate unknown genetic sequences. In either embodiment, the combination of the frameshifting sequence(s) and other coding sequences or gene sequence is understood as the polynucleotide of the claimed invention. The building block depicted at the bottom of FIG. 5 is one example of the polynucleotide sequence of the invention. It is understood that this is only one embodiment of the invention. For example the invention also includes but is not limited to, the following variations of the building block in FIG. 4, namely the random DNA could be replaced with DNA for a known gene, more than one ribosomal frameshifting sequence could be used, or the coding DNA could be separated by one or even by more than one frameshifting sequence. Construction of this building block or polynucleotide sequence of the claimed invention is discussed more fully below.

In a preferred method of practicing the invention it is necessary to select for a specific frameshifting sequence (i.e. a mixer, switch, splitter, etc.) and then operably link this sequence to a genetic sequence of interest to form the polynucleotide of the claimed invention. The first step in selection of a specific frameshifting sequence is the construction of a vector. A skilled artisan may apply various technologies in the construction of a vector. Further, one skilled in the art will understand that there are numerous vectors that might be used to practice the present invention. In a preferred approach, the skilled artisan will use a filamentous phage vector, such as the M13 vector or one of its derivatives (for example the Fd or F1 vectors), or a phagemid vector such as the pCANTAb5E vector. Several references, which may be addressed to learn standard molecular biological procedures, include Sambrook et al. (1989) *Molecular Cloning*, second edition, Cold Springs Harbor Laboratory, Plainview; N.Y.; and R. Wu (ed.) *Methods in Enzymology* 100 and 101.

a. Vector Selection

The first step in constructing a vector that enables the skilled artisan to practice the claimed invention is the selection of an appropriate vector. In the preferred approach, the essential elements of the vector are (1) a sequence encoding an epitope recognized by a monoclonal antibody (MAb), (2) a cloning site for the candidate frameshifting sequence or sequences, and (3) the gene sequence coding for the coat protein of a phage. One example of an epitope that might be used is the FLAG epitope. One of ordinary skill in the art will understand that digesting a nucleotide sequence of interest with various restriction endonucleases described earlier can generate a cloning site. One example of a cloning site is schematically shown in FIG. 7. One example of a suitable gene sequence coding for the coat protein of a phage would be gene III of the M13 bacteriophage. This gene codes for the pIII or the minor coat protein. Also one example of a vector that might be selected and engineered to contain the above elements is the pCANTAb5E phagemid vector.

In one embodiment of the invention the vector is a modified pCANTAb5E phagemid from Amersham-Pharmacia. In this embodiment, the phagemid is further modified by cloning an insert between the SfiI and NotI sites. The insert contains a nucleotide sequence encoding the FLAG epitope (Hopp etal., 1988), two restriction sites, BglII and KpnI, to be used in further manipulation and will carry a large "stuffer" fragment to isolate linearized phagemid DNA and to eliminate the presence of the wild-type pCANTAb5E in the libraries. The sequence of the cloning site in this embodiment is schematically shown in FIG. 7.

Further in this embodiment, the vector constructed is phagemid type A1 shown in FIGS. 4 and 7. The vector contains a 2 kb "stuffer" fragment of any long gene (such as the 500–2500 nt region of the lacZ gene of *Escherichia coli*) which is PCR amplified with two primers. The sequence of the upstream primer includes the SfiI and KpnI sites and the FLAG sequence, and the sequence of the downstream primer includes the BglII and NotI sites. The fragment is cloned into pCANTAb5E precut with NotI and SfiI and the sequence is confirmed by DNA sequencing of the cloning region.

Still further in this embodiment, the two other types of phagemids, type A2 and A3, are constructed in a similar fashion, except the sequence of the PCR primer containing the KpnI site includes an additional two or one nucleotides, respectively. This is depicted in FIG. 7. In this embodiment, vector A2 allows for selection of sequences that cause the +1 frameshift, and vector A3 allows for the selection of sequences that cause the −1 frameshift.

b. Vector Construction

Preferably, for any given candidate frameshifting sequence, one skilled in the art can construct a vector that positions the epitope sequence in the reading frame 0, +1, or −1 with respect to the frameshifting sequence. Further it is preferred that the vector be constructed so that the gene encoding the coat protein (gene III in this example) can be positioned in any of the three reading frames, 0, +1, or −1, with respect to the frameshifting sequence.

This preferred method of vector construction is diagrammed in FIG. 4 and leads to the creation of nine different vectors. It is understood that the nine vectors will differ in the number of nucleotides between the epitope sequence and the cloning site, as well as differ in the number of nucleotides between the cloning site and coat protein gene. It is described below, and further understood that, by utilizing these nine vectors in a specific order, one skilled in the art is able to select for a specific type of frameshifting sequence.

1. Selection for Switch Frameshifting Sequence

For example, in a preferred embodiment of the invention, one skilled in the art may select a simple +1 switch frameshifting sequence by cloning a random DNA sequence of given length, for example 21 nucleotides, into the B1 vector, as depicted in FIG. 4. According to techniques well known in the art, one skilled in the art prepares phage to contain the B1 vector and then biopans the prepared phage against the anti-epitope MAb. In one example, the anti-epitope MAb is the anti-FLAG MAb. For the phage to bind to solid phase, the phage must have the FLAG fused to the coat protein. The requirement for the phage binding, therefore, is to have the frameshifting to occur because the length of the inserted sequence between the FLAG (selected by the target anti-FLAG MAb) and the gene III protein (required for display on the phage particle) is not constructed as a multiple of three nucleotides. It is understood that in this example, the approach is different than in a typical phage display experiment. The selection is not for clones binding to the anti-FLAG MAb (they all have the FLAG expressed), but for events leading to a protein fusion between the FLAG sequence and the coat protein. It is further understood that this approach will result in some insert sequences supporting only standard (i.e. non-frameshifted) translation, and might not yield any phage displaying the epitope sequence, as the gene III sequence will be out of frame in the B1 vector. It is still further understood that the only phage capable of binding to the MAb will be those carrying the insert for a +1 switch frameshift. It is also understood that biopanning means the selection of peptides or proteins with desired binding properties.

One of ordinary skill in the art will appreciate that this scheme might yield false positive clones that have the DNA insert truncated by one or two nucleotides, or extended by one or two nucleotides. Such false positive clones would look like the regular in-frame fusions of the FLAG and the coat protein. A way to address the problem could involve: 1) using synthetic DNA of extremely high purity, or 2) having another biological selection step for the proper length of the insert, such as cloning the insert in the reverse orientation into the phage system and demanding uninterrupted translation from the FLAG sequence into the gene III.

One example of how the skilled artisan may select for a switch frameshifting sequence involves the use of a phage display system. This example involves dilution of the anti-FLAG MAb in 50 mM sodium carbonate buffer, with an initial pH of 9.5 to a final concentration of 1 $\mu$g/mL, which is then adsorbed to the wells of a microtiter plate overnight at 4° C. The wells are then blocked with PBS containing a 2% non-fat dried milk (MPBS) at room temperature for one hour. Library phage are diluted in MPBS, incubated for thirty minutes at room temperature, and then 100 $\mu$L are added per well. Input phage titer for the first round is ~$10^{13}$ cfu/ml, while for the second and third rounds ~$10^{11}$ cfu/ml is used and 8 wells per round. The plate is incubated at room temperature for 2–3 hours, and then washed thirteen times with 200 $\mu$l/well of MPBS. Bound phage are eluted in 100 $\mu$l/well of 20 mM glycine-HCl pH 2.2, for 30 seconds, and then neutralized with Tris-HCl pH 8.0. The eluted phage is used to infect log phase TG1 cells and then plated onto agar plates containing 2xYT/ampicillin/glucose, and incubated overnight at 30° C. Cells are scraped off and stored in 10% glycerol at −80° C. For the next panning round, phage is rescued from these cells in culture as described above, except that the bacteria are incubated after helper phage is added for only 30 minutes with gentle shaking, and the precipitated phage is resuspended in MPBS. The number of biopanning rounds needed is between 1 and 4. The phagemid sequences are then determined by DNA sequencing and characterized. The sequences will be analyzed for their consistency with the design of the splitter insert, DNA sequence patterns, consensus sequences, presence or absence of the stop codons, nucleotide composition, and other characteristics.

2. Selection for Three Way Splitter Frameshifting Sequence

In another preferred embodiment of the invention, one skilled in the art may select for a three way splitter frameshifting sequence. In the preferred method, the skilled artisan will use the vector construct described above. More specifically, one skilled in the art may select a three way splitter frameshifting sequence by cloning a random DNA sequence of a given length, again say 21 nucleotides, into the B1 vector described above. As described above, the skilled artisan, using techniques well known in the art, prepares phage to contain the B1 vector and then biopans the prepared phage against anti-epitope MAb. The insert (i.e. the random 21 nucleotide DNA sequence) is then recloned into the C1 vector, phage is again prepared and a second round of biopanning against the anti-epitope MAb is carried out. The insert is now recloned into vector A1, phage is again prepared and a third round of biopanning against the anti-epitope MAb is carried out. The DNA insert sequence isolated in the third round of biopanning contains the three way splitter frameshifting sequence.

In another preferred embodiment of the invention, one of ordinary skill in the art may use an alternative method to select for a splitter frameshifting sequence. In an alternative method, the skilled artisan will biopan phage from the A2-type library of potential frameshifting sequences against the anti-FLAG monoclonal antibody. Preferably two rounds of biopanning are performed. Further, the eluted phage from the second round of biopanning are preferably transfected into *Escherichia coli*. The cells are then grown, harvested and preferably phagemid DNA is prepared. The phagemid DNA is preferably digested with the BglII-KpnI restriction fragment (preferably a pool of different DNA sequences) is isolated and cloned into the type A3 phagemid vector. The A3-type phage are then grown, and the biopanning procedure is repeated. Preferably, in the third selection step, the DNA from step two is recloned into vector type A1 and biopanning is performed. In the alternative three step embodiment, one of ordinary skill in the art preferably obtains DNA sequences which cause the ribosome to shift frames from the incoming reading frame 0 to any of the three outgoing reading frames.

A further preferred embodiment of the invention utilizes ELISA analysis to detect phage clones. This selection method is discussed more fully in the examples.

3. Selection for Mixer Frameshifting Sequence

In another preferred embodiment of the invention, one skilled in the art may select for a mixer frameshifting sequence. This selection process requires that the random DNA sequence of a given length be cloned into all nine vectors described in FIG. 4, as well as undergo biopanning steps for selection between being cloned into each vector, as described above for vectors A1, B1, and C1.

A skilled artisan may apply various technologies to characterize the frameshifting sequences obtained by using the method described above. One example of an applicable technology would be utilization of an expression system employing an enzyme fusion, such as the β-galactosidase expression system (Goldman et al., 2000). Utilization of an expression system or enzyme assay to analyze or characterize the isolated frameshifting sequence is discussed more fully in the examples. Aside from characterizing the frameshifting sequence, this system also allows one skilled in the art to establish the translational efficiency of the selected frameshifting sequence.

In a further preferred embodiment for selection of the ribosomal frameshifting sequence, the polynucleotide composition is skewed toward G (guanosine) and T (thymidine) residues. The skilled artisan will understand that a high G:T content could lead to a higher propensity of mRNA to form secondary structures, due to G:U base pairing, similar to the earlier referenced RNA pseudoknot, capable of causing ribosomal frameshifting.

B. Construction of Polynucleotide Sequence of the Present Invention

The skilled artisan may apply various technologies in engineering the olynucleotide sequence of the invention. This polynucleotide sequence must contain at least one ribosomal binding site and at least one ribosomal frameshifting sequence within a genetic sequence that is either known or unknown.

1. Selection of Ribosomal Frameshifting Sequence

One method for constructing this polynucleotide sequence involves the assembly of restriction fragments. The first step is to select a frameshifting sequence, as described above. One frameshifting sequence that might be selected is a mixer frameshifting sequence. One skilled in the art may apply various technologies well known in the art to connect the mixer frameshifting sequence to a random coding DNA sequence. For example, the skilled artisan will understand that it is possible to cleave the random coding DNA sequence at certain restriction sites and then ligate the selected ribosomal frameshifting sequence to the cleaved random DNA to form a single sequence. The random coding DNA sequence can be an ensemble of as few as two and up to as many as $10^{15}$ or more different sequences.

2. Preparation of Cloning Vector

In this approach, the next step is the preparation of the cloning vector. The cloning vector yields the polynucleotide sequence of the invention and is diagrammed in FIG. 5. The important elements of the cloning vector are the restriction sites. In one example of a cloning vector, the restriction sites are FokI, BglII, and KpnI. The mixer, or other selected frameshifting sequence, is flanked by KpnI and FokI restriction sites and a "stuffer DNA" as shown in FIG. 5. A stuffer DNA is understood to mean any DNA sequence that is long enough (approximately 10 base pairs (bp) to 3,000 base pairs (kbp)) to enable efficient purification of the linearized form of the vector. The cloning vector is then digested with BglII and KpnI restriction endonucleases and the linearized form is purified. Next a synthetic oligonucleotide with a highly variable (meaning random) sequence throughout much of its length, but not at both ends (4 nucleotides from each end is the sequence that enables cloning into the vector) and not at protruding FokI ends, is ligated to the linearized vector. Ligation of DNA sequences is a common and well understood technique in the art. One skilled in the art may add a DNA polymerase to fill in the product of the ligation and then again ligate the DNA. The ligated DNA is then introduced into *Escherchia coli* via the well understood and common electroporation technique. The skilled artisan may isolate the DNA by applying various technologies in the art.

The isolated DNA is then digested with the FokI restriction endonuclease. The DNA sequence yielded by this method is one example of a polynucleotide sequence that might be used to practice the present invention.

3. Alternative Methods for Engineering Polynucleotide of the Invention

It is also understood that in another preferred embodiment of the invention, the random DNA is replaced with a known coding sequence for a target protein. It is further understood that the polynucleotide of the present invention can be engineered to contain ribosomal frameshifting sequences by several methods, including but not limited to mutation and digestion with restriction endonucleases.

Figure 2:
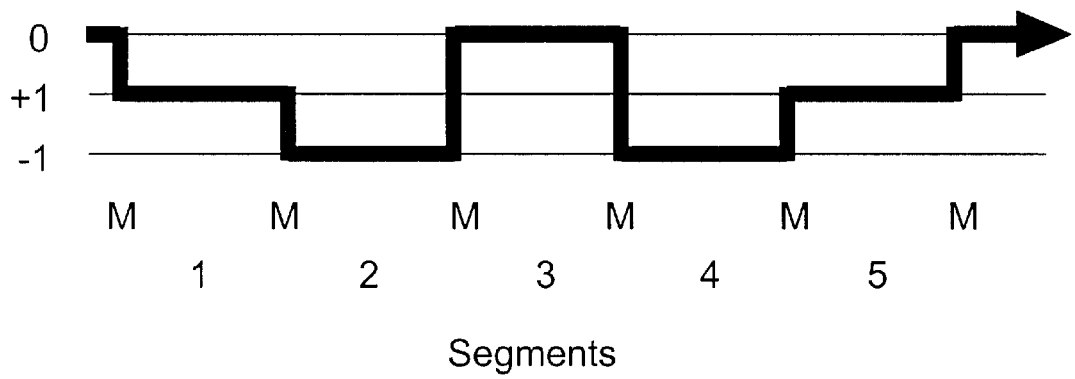
FIG. 2. Illustration of the concept of combinatorial translation. The ribosome "makes a decision" at each mixer sequence (M) or splitter sequence (S) regarding which reading frame to use. The black line represents an example of the translation route initially translated in the 0 frame, then segment 1 is translated in the +1 frame, followed by a frameshift to the −1 reading frame, segment 3 is read in the 0 frame, etc., leading to the (0, +1,−1, 0, −1,+1, 0) translation product.
Figure 3:
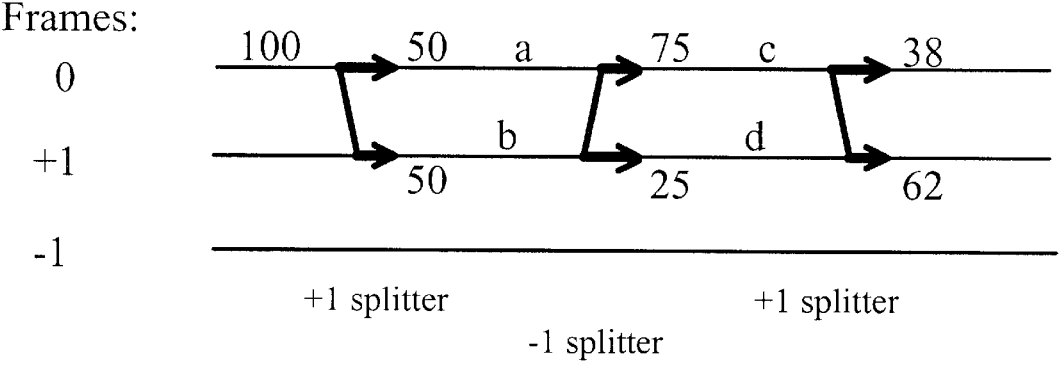
FIG. 3. Hypothetical effects of splitters on translation. The figure indicates the relative translation rate in three reading frames. The incoming translation is 100. Splitters are assumed to direct the translation evenly between two reading frames with no loss of ribosomes. The second and the third splitters affect the translation by the ribosomes incoming in the +1 and 0 frame, respectively, according to the definition of the splitter. Translation of the gene fragment shown results in production of three protein products, namely ac, bc and bd, rather than one protein product as usually expected. This simple pattern converges after a few more splitters to the alternating 33:67 or 67:33 split of the ribosomes between the two reading frames, and could be repeated many times within a gene.

4. Polynucleotide of the Invention Containing One Ribosomal Frameshifting Sequence Versus a Polynucleotide of the Invention Containing Two or More Ribosomal Frameshifting Sequences In a preferred embodiment of the invention, at least one of the ribosomal frameshifting sequences is inserted into the coding sequences of a gene. In another preferred embodiment of the invention, two or more of these ribosomal frameshifting sequences are inserted into the gene. One advantage of inserting multiple frameshifting sequences is that the number of possible translation routes grows exponentially with the number of frameshifting sequences. This type of translation is known as combinatorial translation. One example of this is depicted in FIG. 2, which shows the translational pathway of a ribosome that encounters six mixer sequences. As the ribosome encounters each frameshifting sequence, it is shifted to a different reading frame. If a gene encoding the translational pattern depicted in FIG. 2 were cloned in a phagemid and the phagemid were subsequently introduced into *Escherchia coli*, then a single *Escherichia coli* cell would produce and display up to 243 different recombinant proteins produced from a single genetic sequence. In the prior art, a single genetic sequence could produce numerous but only identical peptides or proteins.

C. Boundaries on Construction of Polynucleotide Sequence of the Invention

It is understood that in constructing (or cloning) the polynucleotide sequence to be utilized in the present invention, it is necessary to use appropriate cloning vector. A skilled artisan may apply various technologies to the polynucleotide sequence so that it will be clonable in the given vector. In one example, if the polynucleotide sequence were composed of mRNA, the skilled artisan could use the enzyme reverse transcriptase to make cDNA. It is understood that the cDNA will be complementary to the mRNA sequence that served as the template. Also common and well understood in the art are techniques for creating single or double stranded DNA or cDNA. These techniques are outlined and described in K. Doyle (ed.) *Promega: Protocols and Applications Guide*, third edition, pages 180–84, and are herein incorporated by reference.

It is further understood that the polynucleotide sequence will cause translational events to occur in the cell and the polynucleotide sequence should be viewed as a type of "program" that the cellular ribosome reads and this "program" causes the ribosome to shift the reading frame.

It is still further understood that the polynucleotide sequence is non-naturally occurring and is connected to a heterologous promoter. One skilled in the art specifically engineers the polynucleotide sequence to contain the ribosomal frameshifting sequences and further the skilled artisan utilizes a foreign or synthetic promoter to transcribe the message of the polynucleotide sequence.

D. Utilities of the Polynucleotide Sequence of the Present Invention

The polynucleotide sequence of the present invention has numerous utilities. For example by engineering a vector to contain the polynucleotide sequence of the invention, one skilled in the art would then be able to construct a combinatorial library or more simply a phage library. In a preferred embodiment, the skilled artisan would create a combinatorial library of randomized peptides on filamentous phage. Both phage and combinatorial libraries are good sources of information regarding ligands for proteins, the structure and function of proteins, and protein-protein interactions. Typically in either type of library, phage carries the recombinant peptide fused to the minor coat protein, pIII and the DNA encoding the recombinant peptide is cloned into gene III of the phage.

1. Construction of a Phage Library

There are two general designs from which one of ordinary skill in the art is able to choose, in constructing a phage library. In one embodiment, the skilled artisan will clone the DNA encoding the polynucleotide sequence of the invention into the gene III of the phage. It is understood that, in principle, this approach leads to every copy of the pIII protein (expressed from gene III) being fused to the recombinant peptide translated from the polynucleotide sequence.

In the preferred embodiment and alternative design, the skilled artisan will use a phagemid vector, which contains only the gene III sequence and an origin of replication. The polynucleotide sequence is inserted into the coding sequences of gene III. This phagemid is then introduced into *Escherichia coli* host strain, and then rescued by superinfection with helper phage, which helper phage preferably has a weakened origin of replication. It is understood that this technique will cause the phage selected or saved during superinfection to preferentially contain the phagemid, rather than the helper phage, DNA. It is also understood that in this approach, the pill protein is made from both wild-type helper phage and the peptide-coat protein fusion gene on the phagemid.

It is understood that both designs can be used to construct the phage library of the present invention. However the latter approach is preferred because expression of the wild-type pIII protein effectively dilutes the proportion of fusion protein and can thereby be advantageous in reducing selection against polypeptides deleterious to phage growth, thus increasing the diversity of the library. See, e.g., Garrard, WO 92/09690.

Aside from the simple phage library described above, the present invention can also be utilized in the construction of a new type of phage library, a combinatorial library, in which the phage-displayed protein is encoded by the gene having alternating frameshifting and random nucleic acid sequences. Thus a single *Escherichia coli* cell will make significantly more than one type of recombinant polypeptide per cell.

a. Construction of a Combinatorial Library

*Escherichia coli* can make and store up to $10^7$ protein molecules in a single cell. The cell engineered for expression of a single heterologous gene can produce up to 70% of all proteins made in the cell as identical copies of the protein encoded by the heterologous gene (Bolling and Mandecki, 1990). The present invention takes advantage of the ability of *Escherichia coli* to produce so many proteins but the advantage of the invention is that a single *E.coli* cell is able to produce a plurality of peptides, rather than millions of copies of a single type of peptide. These peptides form the combinatorial library of the invention.

Figure 6:
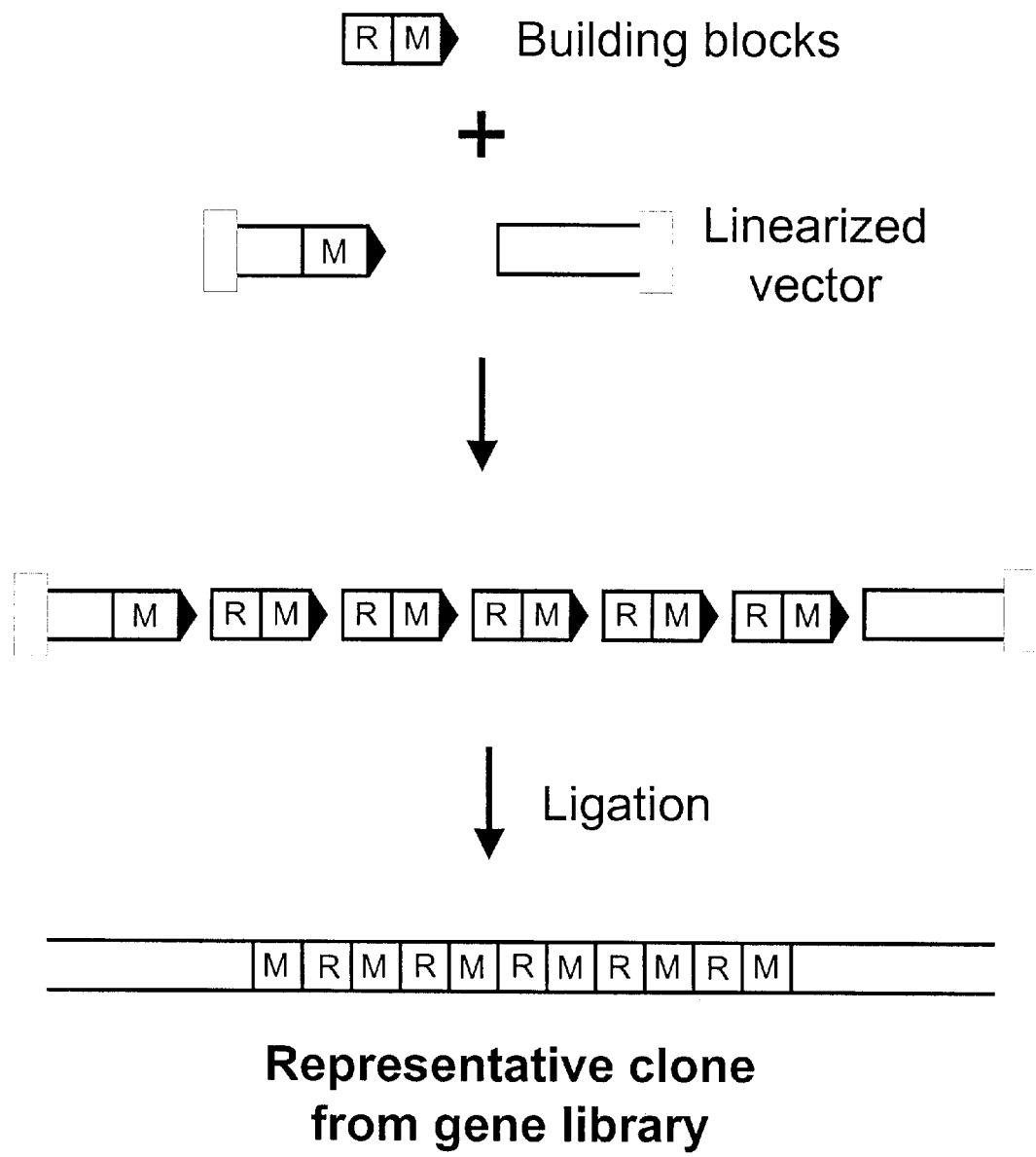
FIG. 6. Making of gene library. A scheme to obtain a representative clone from the gene library from the building blocks and a linearized vector.

In a preferred embodiment for construction of a combinatorial library, an assembly vector, preferably a phagemid, phage or plasmid, is constructed. However before construction of the vector, the polynucleotide sequence of the invention must be constructed as detailed above. Preferably in the vicinity of the cloning site the assembly vector contains a mixer ribosomal frameshifting sequence followed by a restriction nuclease site producing ends compatible with the first FokI cleavage site (described above in the formation of the polynucleotide sequence of the invention), followed by spacer DNA and another restriction nuclease site producing protruding ends compatible with the second FokI cleavage site. One example of a restriction endonuclease capable of generating FokI-compatible ends is BsbI. Preferably, the assembly vector will produce a polynucleotide restriction fragment with two unique ends, preferably CCCC and GGGG. This will cause the restriction fragment to ligate to itself, under appropriate conditions, with a controlled directionality, meaning only head-to-tail ligation and not head-to-head or tail-to-tail ligation (Mandecki and Bolling, 1988). This also provides the advantage of the polynucleotide ligating to the assembly vector with a controlled directionality. The number of polynucleotide sequences per vector can be controlled by the relative amounts of DNA and the ligation conditions of the reaction. FIG. 6 depicts several of these polynucleotide sequences, also called building blocks, ligated together to form the genetic sequence of a clone in a combinatorial library. This embodiment is further discussed in the examples.

In an alternative technique, the precise length of the combinatorial gene can be controlled. To accomplish this, ligation of the polynucleotide to the assembly vector is done in three phases. First one of ordinary skill in the art will assemble the polynucleotide sequences or building blocks only in ligation conditions that limit the length of the ligated DNA. The skilled artisan will then use agarose or polyacrylamide gel electrophoresis and purification to isolate a fragment having the desired length. Finally one of ordinary skill in the art will ligate the assembled combinatorial gene, composed only of fragments of the desired length, into the assembly vector.

In a further preferred embodiment, the skilled artisan can assure translation of the random regions and the mixer sequences in all three reading frames by avoiding stop codons. In one example, the skilled artisan will only use sequences without T (thymidine) nucleotides. It is understood that this will eliminate all stop codons as well as reduce the number of amino acids that might be incorporated in a polypeptide chain from 20 to 16. However, the skilled artisan will appreciate that this will not have a significant adverse effect on the quality of the library.

In another preferred embodiment, the skilled artisan might construct the random region by using selected trinucleotide phosphoramidites for the codons. It is understood that choosing trinucleotide sequences that end with neither a T nucleotide, nor a TA dinucleotide, nor a TG dinucleotide, for the synthesis of oligonucleotides enables the synthesis of gene sequences encoding 19 amino acids (all the natural amino acids with the exception of methionine). One example of a set of codons for the 19 amino acids is the following group: Ala GCC, Arg CGC, Asn AAC, Asp CAC, Cys TGC, Gln CAA, Glu CAG, Gly GGC, His CAC, Ile ATC, Leu CTC, Lys AAA, Phe TTC, Pro CCC, Ser TCC, Thr ACC, Trp TGG, Tyr TAC, Val GTC.

1) Alternative Library Construction

It is understood that many types of libraries, other than phage and combinatorial, can be formed utilizing the polynucleotide sequence of the invention. In one embodiment, the expression product might be a soluble protein localized in the cytoplasm of a cell, and selection could then be applied to assess the regulation of cell metabolism or enzymatic activity. In an alternative embodiment, the expressed product can be anchored to the cell wall outer surface, and selected for interactions with other cells or biomolecules; in this example, the expressed product may be secreted by the cell and selected for activity in locations either proximal or distant to the cell. One of ordinary skill in the art will also understand that it would be possible to construct a new type of polysomal library, where the polynucleotide sequence of the invention is translated in vitro. This means that translation of the mRNA in vitro would be combined with retention of the nascent ribosome-mRNA-peptide complex.

1. Selection of Targeted Proteins from Combinatorial Library

A preferred method of selecting genes from a combinatorial library is by phage display. The combinatorially-translated genes in the library are recloned into a phage vector or a phagemid vector by standard methods (Kay et al., 1996), the phage is grown and the resulting phage library is subjected to biopanning against a molecule, preferably a biomolecule, such as a protein, antibody, DNA, or a small organic molecule. It is important to note that even inorganic molecules in a form of solid phase (e.g. ice, solid forms of carbon) are suitable targets. One or more rounds of biopanning may be needed to achieve an appropriate level of enrichment. Then the genes emerging from biopanning are sequenced and analyzed.

It is understood that an important facet of the present invention is the ability to deduce the sequences of the combinatorially translated proteins from the combinatorial library. It is further understood that translation is proceeding in different reading frames over the length of the gene, so there may be no one-to-one correspondence between the gene sequence and the protein sequence, as is commonly seen in standard libraries. One of ordinary skill in the art will understand that there are several techniques available for sequencing the proteins isolated from the combinatorial library. Some examples of such techniques include but are not limited to, identification of consensus sequence(s), deletion analysis, mutational analysis, (similar to that in Carcamo et al. (1998)) or if the product of the combinatorial translation can be expressed in the cell and purified, the precise determination of the molecular weight by mass spectrometry (in conjunction with the known DNA sequence) to identify the amino acid among the numerous possibilities.

3. Construction of Phage

A further preferred embodiment of the invention is a phage containing the polynucleotide sequence of the invention. Preferably the phage is engineered to have an origin of replication, a selectable marker, suitable restriction sites, and the polynucleotide sequence of the invention. More preferably, the phage is engineered so that the skilled artisan can clone a genetic sequence of interest into the phage and then express the phage to obtain a plurality of peptides from that genetic sequence of interest. In one embodiment the genetic sequence is for a known gene or protein. In another embodiment, the genetic sequence is unknown. Preferably, the restriction sites of the phage are not inserted in indispensable genes of the phage. It is understood that this would lessen the viability of the phage and the cloning would be less successful. A six nucleotide restriction enzyme cleavage site will occur on average every $4^6$ base pairs (i.e. approximately every 4 kilo base pairs). Preferably, the size of the phage DNA is limited because it is understood that larger DNA sequences are more difficult to handle and therefore more liable to be damaged. Also, preferably the cloning site is in a functional sequence.

The following examples are provided for illustrative purposes and are not intended to limit the scope of the invention as claimed herein. Any variations in the exemplified compositions and methods that occur to the skilled artisan are intended to fall within the scope of the present invention. Abbreviations and nomenclature used throughout are standard in the field.

EXAMPLE 1

Construction of DNA library of Frameshifting Sequences

The method to construct the library of frameshifting sequences is chosen to minimize the presence of deletion or insertion sequences, typically present in such libraries as a result of chemical modification during oligonucleotide synthesis, or as a result of errors accumulated during PCR. Therefore, the shortest possible synthetic oligonucleotides are used. The cloning method used is not based on PCR. A 29 nt oligonucleotide (29 nt=21 nt for the frameshifting sequence plus 2×4 nt for the protruding ends for cloning) is made and purified to a high purity standard using HPLC and PAGE. Phagemid A2 is cut with BglII and KpnI, and the linearized large DNA fragment is purified on an agarose gel. The oligonucleotide is ligated to linearized DNA in ligation buffer (New England Biolabs), creating a gap in the circular double-stranded DNA as shown in FIG. 7. The gap is filled in an extension reaction with Klenow polymerase. The DNA product is desalted by running a desalting column (Qiagen) and introduced into electrocompetent *Escherichia coli* cells by electroporation. Ten µg or more of ligated phagemid DNA is used in 100 electroporations, each based on 100 µl volume of electrocompetent cells, using 20 µg DNA per one electroporation. A small aliquot will be used for titering. The cells are then transferred to 2 L of the liquid 2×YT-AG medium and grown to the late logarithmic phase for about 6 hours. The late logarithmic-phase culture is plated to obtain individual colonies with the purpose of establishing the efficiency of transformation, and of picking colonies for sequencing. Aliquots of the culture are centrifuged, the cells are resuspended and frozen to constitute stocks of the phagemid library. The remaining cell culture will be grown overnight, and cells harvested by centrifugation. Plasmid DNA is prepared using a Qiagen Plasmid Mega Kit, aliquoted and kept frozen, creating a DNA form of the frameshifting sequences in the phagemid library. Phage from the phagemid library (*Escherichia coli* cells) are then rescued using a standard procedure involving helper phage, as described below. The resulting phagemid library is amplified by adding the entire transformation culture to 4 L of 2×YT-AG, and letting the cells grow until the $A_{600nm}$ increased ~400 times. The cells are harvested by centrifugation at 3000×g for 20 minutes, then resuspended in 40 mL of 2×Y-TAG containing 8% glycerol. The library is stored at −80° C. until the phage rescue step is performed.

Preparation of Electrocompetent Cells

For cloning, TG1 electrocompetent cells, prepared as previously described (Ravera et al.,1998), are used in electroporations at 1500 volts; 0.1 mm gap electroporation cuvettes contain 12.4 µg of DNA and 500 µL of TG1 cells. 12.5 ml of prewarmed (40° C.) 2×YT (yeast extract+tryptone) medium containing 2% glucose (2×YT-G) is added immediately following the electric pulse, and the cells are allowed to grow for 1 hour at 37° C. For titering, an aliquot of the transformation culture is plated onto 2×YT-G plates containing 100 µg/mL of ampicillin (2×YT-AG).

Phage Rescue

For library phage rescue, the cells in glycerol are grown in 2×YT-AG culture at 30° C. to an $A_{600nm}$ of 0.5, and then M13KO7 helper phage added at a (multiplicity of infection, MOI) of 15. The culture is incubated at 37° C. first for 30 minutes with shaking at 250 revolutions per minute (rpm), and then for 30 minutes without shaking. After pelleting the cells and removing the supernate containing helper phage, the cell pellet are resuspended in 2×YT-A (no glucose) containing 50 μg/mL kanamycin and grown overnight at −30° C. The culture is then centrifuged at 3000×g for 30 minutes at 4° C. and the supernate containing phage is removed. Phage is precipitated from the supernate with 4% polyethylene glycol (PEG)/0.5 M NaCl (final concentrations) on ice for 1 hour. The precipitate is recovered by centrifugation at 10,000×g for 30 minutes, and the pellet resuspended in phosphate buffered saline (PBS) at 1/100 of the initial culture volume, and filtered through a 0.45 μm filter. Phage is titered by infection of TG1 cells according to the Amersham Pharmacia protocol.

EXAMPLE 2

ELISA Analysis of Phage Clones

Single colonies are picked from plates after biopanning, and the phage is rescued as described above. Enzyme-linked immunosorbent assay (ELISA) microtiter plates are coated with the anti-FLAG MAb and blocked as described above. An irrelevant antibody is used as a control. Phage resuspended in MPBS is added in duplicate at 100 μl/well and incubated at room temperature for 1 hour, then removed and the wells washed 3× with PBS. For detection, anti-M13 antibody conjugated to horseradish peroxidase (Amersham Pharmacia Biotech) is diluted 1:3000 in MPBS and 100 μL added/well. The plate is incubated for 1 hour, then the wells washed with PBS as above. ABTS solution, 100 μl/well (Boehringer) is added, and the color reaction stopped with 0.5% SDS (final concentration) in each well. $A_{405nm}$ is read in a SpectraMax 340 microplate reader (Molecular Devices) using SoftmaxPro software. Background color is subtracted and duplicate readings for each sample are averaged. Clones with readings ≧2 times the background absorbance (and having the DNA sequence of expected length) are considered positives.

LITERATURE CITED

Bolling T J and Mandecki W (1990) An *Escherichia coli* expression vector for high-level production of heterologous proteins in fusion with CMP-KDO synthetase. BioTechniques 8:488–492.

Carcamo J, Ravera M W, Brissette R, Dedova O, Beasley J R, Alam-Moghé A, Wan C, Blume, A, and Mandecki W (1998) Unexpected frameshifts from gene to expressed protein in a phage-displayed peptide library. Proc Natl Acad Sci USA 95:11146–11151.

Cwirla S E, Balasubramanian P. Duffin D J, Wagstrom C R, Gates C M, Singer S C, Davis A M, Tansik R L, Mattheakis L C, Boytos C M, Schatz P J, Baccanari D P, Wrighton N C, Barrett R W, and Dower W J (1997). Science 276:1696–1699.

Goldman E, Korus M, and Mandecki W (2000) Efficiencies of translation in three reading frames of unusual non-ORF sequences isolated from phage display. FASEB J. 14, 603–611.

Hopp T P, Prickett K S, Price V, Libby R T, March C J, Cerretti P, Urdal D L, and Conlon P J (1988). Biotechnology 6:1205–1210.

Kay B K, Winter J and McCafferty J (Eds.) (1996) Phage Display of Peptides and Proteins: A Laboratory Manual. Academic Press, pp.1–344.

Livnah, O, Stura E A, Johnson D L, Middleton S A, Mulcahy L S, Wrighton N C, Dower W J, Jolliffe L K, and Wilson I A (1997) Science 273:469–71.

Lowman, H B (1997) Bacteriophage display and discovery of peptide leads for drug development. Annu. Rev. Biophys. Biomol. Struct. 26:401–424.

Mandecki, W and Bolling T J (1988) FokI method of gene synthesis. Gene 68:101–107.

Mandecki W, Chen Y-C, an,d Grihalde N (1995) A mathematical model for biopanning (affinity selection) using peptide libraries on filamentous phage. J Theor Biol 175:523–530.

Mandecki W, Brissette R, Carcamo J, Cheng, W, Dedova, O, Hsiao, K C, Moghe, A, Ravera, M, Shen, H, Tang, P, and Blume, A (1997). Display Technologies-Novel Targets and Strategies. P. Guttry (ed). International Business Communications, Inc., Southborough, Mass., pp. 231–254.

Ravera M W, Carcamo J, Brissette, R, Alam-Moghe A, Dedova O, Cheng, W, Hsiao K C, Klebanov D, Shen, H, Tang, P, Blume, A, and Mandecki, W (1998) Identification of an allosteric binding site on the transcription factor p53 using a phage-displayed peptide library. Oncogene 16:1993–1999.

Scott J K and Smith G P (1990) Searching for peptide ligands with an epitope library. Science 249:386–390.

Wrighton N C, Farrell F X, Chang R, Kashyap A K, Barbone F P, Mulcahy L S, Johnson D L, Barrett R W, Jolliffe L K, and Dower W J (1996). Science 273:458–463.

Yanofsky S D, Balidwin D N, Butler, J H, Holden, F R, Jacobs, J W, Balsubramanian, P, Cinn, J P, Cwirla S E, Petter-Bhatt, E, Whitehorn, E A, Tate, E H, Akeson, A, Bowlin, T L, Dower W J, and Barrett, R W (1996). Proc Natl Acad Sci USA 93:7381–7386.

I claim:

1. A method of producing a plurality of polypeptides from a single polynucleotide operably linked to a heterologous promoter comprising the step of expressing a single polynucleotide, wherein such polynucleotide comprises at least two ribosomal frameshifting sequences such that said single polynucleotide is capable of producing a plurality of different polypeptides.

2. The method of claim 1, further comprising isolating the plurality of peptides to obtain the combinatorial library of peptides.

3. The method of claim 1, wherein said polynucleotide is DNA.

4. The method of claim 1, wherein said ribosomal frameshifting sequence is a mixer sequence.

5. The method of claim 1, wherein said ribosomal frameshifting sequence is a splitter sequence.

6. The method of clai 1, wherein said ribosomal frameshifting sequence is a switch sequence.

7. The method of claim 1, wherein said polynucleotide is inserted into a vector.

8. The method of claim 7, wherein said vector is a filamentous phage vector.

9. The method of claim 8, wherein said filamentous phage vector is M13.

10. The method of claim 7, wherein said vector is in a microorganism.

11. The method of claim 10, wherein said microorganism is *Escherchia coli.*

12. The method of claim 10, further comprising the step of determining the activity of the peptides by comparing the metabolism or enzymatic activity of the transformed microorganism to wild type microorganism.

13. The method of claim 10, wherein said protein is expressed on the outer surface of a microorganism.

14. The method of claim 1, further comprising the step of detecting the presence of a peptide.

15. The method of claim 14, wherein said detecting comprises contacting the plurality of peptides with another biomolecule.

16. A method of producing a plurality of peptides from a single polynucleotide operably linked to a heterologous promoter comprising the steps of:
   expressing a polynucleotide, wherein such polynucleotide comprises at least two ribosomal frameshifting sequences;

inserting said polynucleotide into a vector in a microorganism; and expressing said peptide on the outer surface of said microorganism such that said single polynucleotide is capable of producing a plurality of different polypeptides.

17. The method of claim 16, further comprising isolating the plurality of peptides to obtain the combinatorial library of peptides.

18. The method of claim 16, wherein said vector is a filamentous phage vector.

19. The method of claim 16, further comprising the step of determining the activity of the peptides by comparing the metabolism or enzymatic activity of the transformed microorganism to wild type microorganism.

20. The method of claim 16, further comprising the step of detecting the presence of a peptide.

21. The method of claim 20, wherein said detecting comprises contacting said combinatorial library with another biomolecule.

* * * * *

UNITED STATES PATENT AND TRADEMARK OFFICE
CERTIFICATE OF CORRECTION

PATENT NO. : 6,440,700 B1
DATED : August 27, 2002
INVENTOR(S) : Wlodek Mandecki

It is certified that error appears in the above-identified patent and that said Letters Patent is hereby corrected as shown below:

<u>Title page,</u>
Item [56], PUBLICATIONS, "W. Mandecki et al." delete "Fok1" and substitute
-- FokI -- in its place.

<u>Column 4,</u>
Line 57, delete "pill" and substitute -- pIII -- in its place.

<u>Column 5,</u>
Line 66, delete "pill" and substitute --pIII -- in its place.

<u>Column 8,</u>
Line 21, delete "Known" and substitute -- known -- in its place.

<u>Column 9</u>
Line 10, delete "ribosbmal" and substitute -- ribosomal -- in its place.

<u>Column 10,</u>
Line 22, delete "pill" and substitute -- pIII -- in its place.
Line 24, delete "pCANTAb5E" and substitute -- pCANTAB5E-- in its place.
Line 27, delete "pCANTAb5E" and substitute -- pCANTAB5E -- in its place.
Line 31, delete "Hopp etal.," and substitute -- Hopp et al., -- in its place
Line 35, delete "pCANTAb5E" and substitute -- pCANTAB5E -- in its place.
Line 45, delete "pCANTAb5E" and substitute -- pCANTAB5E -- in its place.

<u>Column 23,</u>
Line 62, delete "clai 1," and substitute -- claim 1, -- in its place.

Signed and Sealed this

Twentieth Day of May, 2003

JAMES E. ROGAN
*Director of the United States Patent and Trademark Office*

SEQUENCE LISTING

```
<160> NUMBER OF SEQ ID NOS: 12

<210> SEQ ID NO 1
<211> LENGTH: 54
<212> TYPE: DNA
<213> ORGANISM: Escherichia coli
<220> FEATURE:
<221> NAME/KEY: CDS
<222> LOCATION: (25)..(48)

<400> SEQUENCE: 1
```

```
tatgcggccc agccggccat ggcc gac tac aaa gac gat gac gac aaa agatct        54
                         Asp Tyr Lys Asp Asp Asp Asp Lys
                          1               5
```

<210> SEQ ID NO 2
<211> LENGTH: 8
<212> TYPE: PRT
<213> ORGANISM: Escherichia coli

<400> SEQUENCE: 2

```
Asp Tyr Lys Asp Asp Asp Asp Lys
 1               5
```

<210> SEQ ID NO 3
<211> LENGTH: 27
<212> TYPE: DNA
<213> ORGANISM: Escherichia coli
<220> FEATURE:
<221> NAME/KEY: CDS
<222> LOCATION: (16)..(27)

<400> SEQUENCE: 3

```
ggtaccgcgg ccgca ggt gcg ccg gtg                                          27
                 Gly Ala Pro Val
                  1
```

<210> SEQ ID NO 4
<211> LENGTH: 4
<212> TYPE: PRT
<213> ORGANISM: Escherichia coli

<400> SEQUENCE: 4

```
Gly Ala Pro Val
 1
```

<210> SEQ ID NO 5
<211> LENGTH: 16
<212> TYPE: DNA
<213> ORGANISM: Escherichia coli

<400> SEQUENCE: 5

```
ggtaccaagc ggccgc                                                         16
```

<210> SEQ ID NO 6
<211> LENGTH: 15
<212> TYPE: DNA
<213> ORGANISM: Escherichia coli

<400> SEQUENCE: 6

```
ggtaccagcg gccgc                                                          15
```

<210> SEQ ID NO 7
<211> LENGTH: 12
<212> TYPE: DNA
<213> ORGANISM: Escherichia coli

<400> SEQUENCE: 7

```
gacaaaagat ct                                                             12
```

<210> SEQ ID NO 8
<211> LENGTH: 14
<212> TYPE: DNA
<213> ORGANISM: Escherichia coli

<400> SEQUENCE: 8

```
ggtaccgcgg ccgc                                                        14

<210> SEQ ID NO 9
<211> LENGTH: 11
<212> TYPE: DNA
<213> ORGANISM: Escherichia coli

<400> SEQUENCE: 9
gatcttttgt c                                                           11

<210> SEQ ID NO 10
<211> LENGTH: 13
<212> TYPE: DNA
<213> ORGANISM: Escherichia coli

<400> SEQUENCE: 10
gcggccgcgg tac                                                         13

<210> SEQ ID NO 11
<211> LENGTH: 11
<212> TYPE: DNA
<213> ORGANISM: Escherichia coli
<220> FEATURE:
<221> NAME/KEY: modified_base
<222> LOCATION: (6)
<223> OTHER INFORMATION: variable nucleotide

<400> SEQUENCE: 11
gatctnggta c                                                           11

<210> SEQ ID NO 12
<211> LENGTH: 27
<212> TYPE: DNA
<213> ORGANISM: Escherichia coli
<220> FEATURE:
<221> NAME/KEY: modified_base
<222> LOCATION: (13)
<223> OTHER INFORMATION: variable nucleotide

<400> SEQUENCE: 12
gacaaaagat ctnggtaccg cggccgc                                          27
```